United States Patent [19]

Shiao

[11] Patent Number: 5,201,779
[45] Date of Patent: Apr. 13, 1993

[54] DISPOSABLE IMPLANT INJECTOR

[76] Inventor: I-Sen Shiao, 1F, No. 1, Alley 17, Lane 111, Fu-Hsing S Rd. Sec. 2, Taipei, Taiwan

[21] Appl. No.: 835,248

[22] Filed: Feb. 13, 1992

[51] Int. Cl.$^5$ ................................................ A61F 2/76
[52] U.S. Cl. ........................................ 623/66; 604/59; 604/60; 623/8
[58] Field of Search ............... 604/59, 60; 623/11, 623/8, 7, 66

[56] References Cited

U.S. PATENT DOCUMENTS

| | | | |
|---|---|---|---|
| 2,754,822 | 7/1956 | Emelock | 604/59 |
| 3,667,465 | 6/1972 | Voss | 604/60 |
| 4,147,164 | 4/1979 | Behney | 604/60 |
| 4,341,211 | 7/1982 | Kline | 604/60 |
| 4,936,827 | 6/1990 | Grimm et al. | 604/60 |
| 4,955,906 | 9/1990 | Coggins et al. | 623/8 |

Primary Examiner—David Isabella
Attorney, Agent, or Firm—Notaro & Michalos

[57] ABSTRACT

An injector which is applicable for use in mammoplasty, is formed by extrusion and with material having good flexibility. The configuration of the injector includes multiple mutually separatable flaps which each expand outwardly when an implant to be placed in the breast is pressed against the flaps. This is after a guiding rod penetrates into an incision in the skin of the patient so that an implant, pushed by a plunger to pass through the tip of the injector, can be quickly and smoothly placed in a breast. The injector is disposable for completely ruling out infection due to repeated use.

1 Claim, 4 Drawing Sheets

DISPOSABLE IMPLANT INJECTOR

BACKGROUND OF THE INVENTION

The traditional plastic surgery for breast implant involves a cut of incision to the side of the breast, followed with the insertion of a silicone implant behind the breast. This practice is not only time consuming but also very difficult to since it requires to placing an implant with several hundred c.c. of volume through the incision of only several centimeters. Therefore, in 1987, Dr. Peter Eckert designed an implant injector made of stainless steel. This injector is only applicable to implants having smooth surfaces. This injector also has the following characteristics:
1) The injector is made by manual, meaning low production efficiency and high production cost and thus requires disinfection after use for the next occasion. Such a repeated use is very vulnerable to cause infection.
2) The injection tip is very narrow with a fixed diameter, and thus presents a very great resistance when the tip penetrates the patient's skin incision as the implant is about to be placed in the breast by pushing the plunger, and thus making the injection of the implant rather difficult.

Dr. Peter Eckert's injector thus does not overcome various problems in mammoplasty.

SUMMARY OF THE INVENTION

Accordingly, the chief object of the present invention is to provide a disposable implant injector, which, at the tip of the injection barrel, has multiple flaps integrally formed with each flap abutted at one end to the other while mutually breaking away from each other at the farther end so that while the implant is passing through such injection tip each flap expands outwardly to enlarge the outlet and allow a fast and easy insertion of the implant into position for improving the simplicity of and reducing the time required for the operation.

Another object of the present invention is to provide a disposable implant injector, which has an integrally formed barrel, offers a major advance to production and reduction of and cost; furthermore; is disposable for ruling out absolutely any possible infection as may result from the repeated use of the injector.

BRIEF DESCRIPTION OF THE DRAWING

The present invention will become more readily apparent from the following description of the preferred embodiment of the present invention taken in conjunction with the accompanying drawing, in which.

DETAILED DESCRIPTION OF THE PREFERRED EMBODIMENT

Figure 1A:
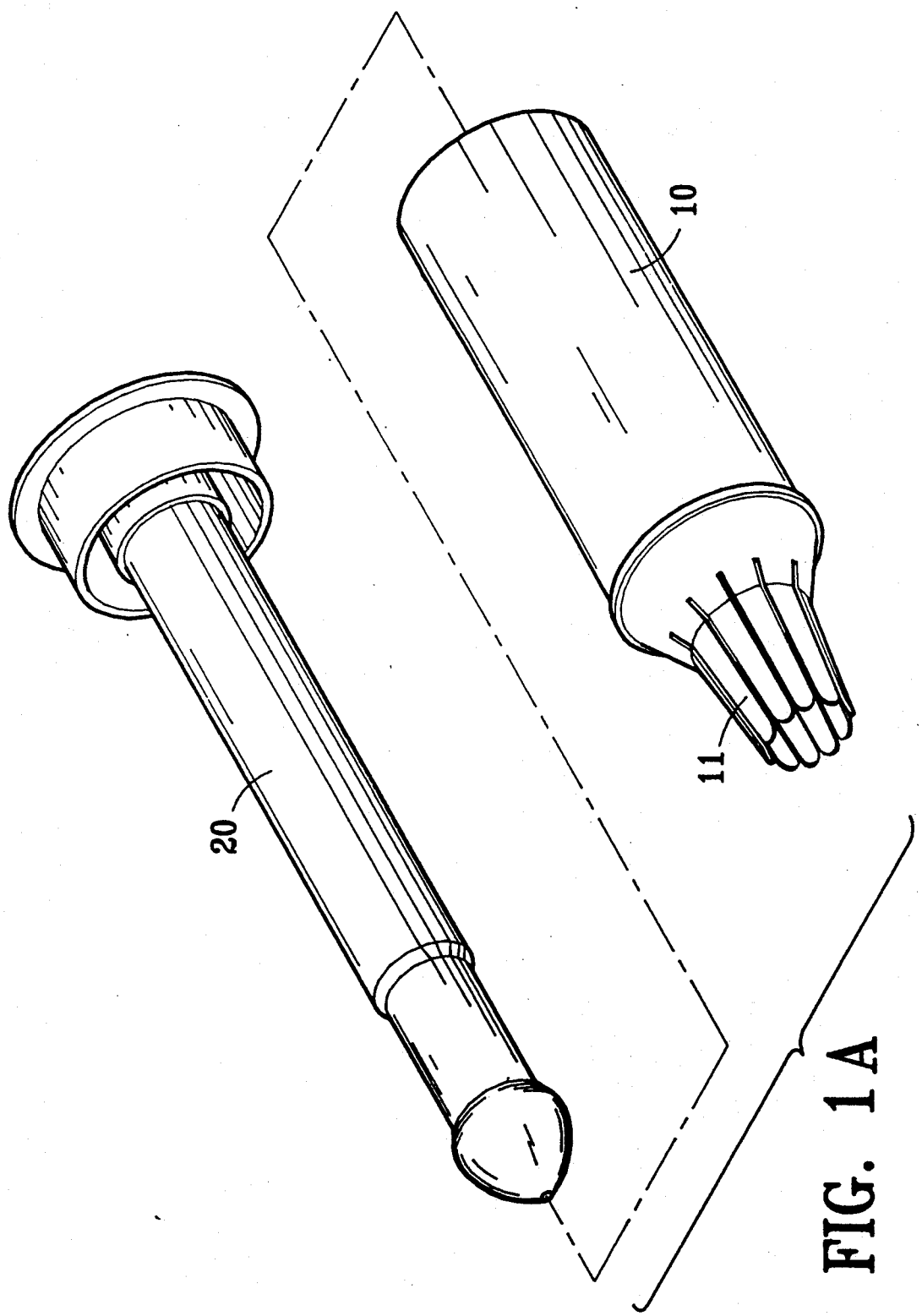
FIG. 1A is a break-down view illustrating the injector and guiding rod of the present invention.
Figure 1B:
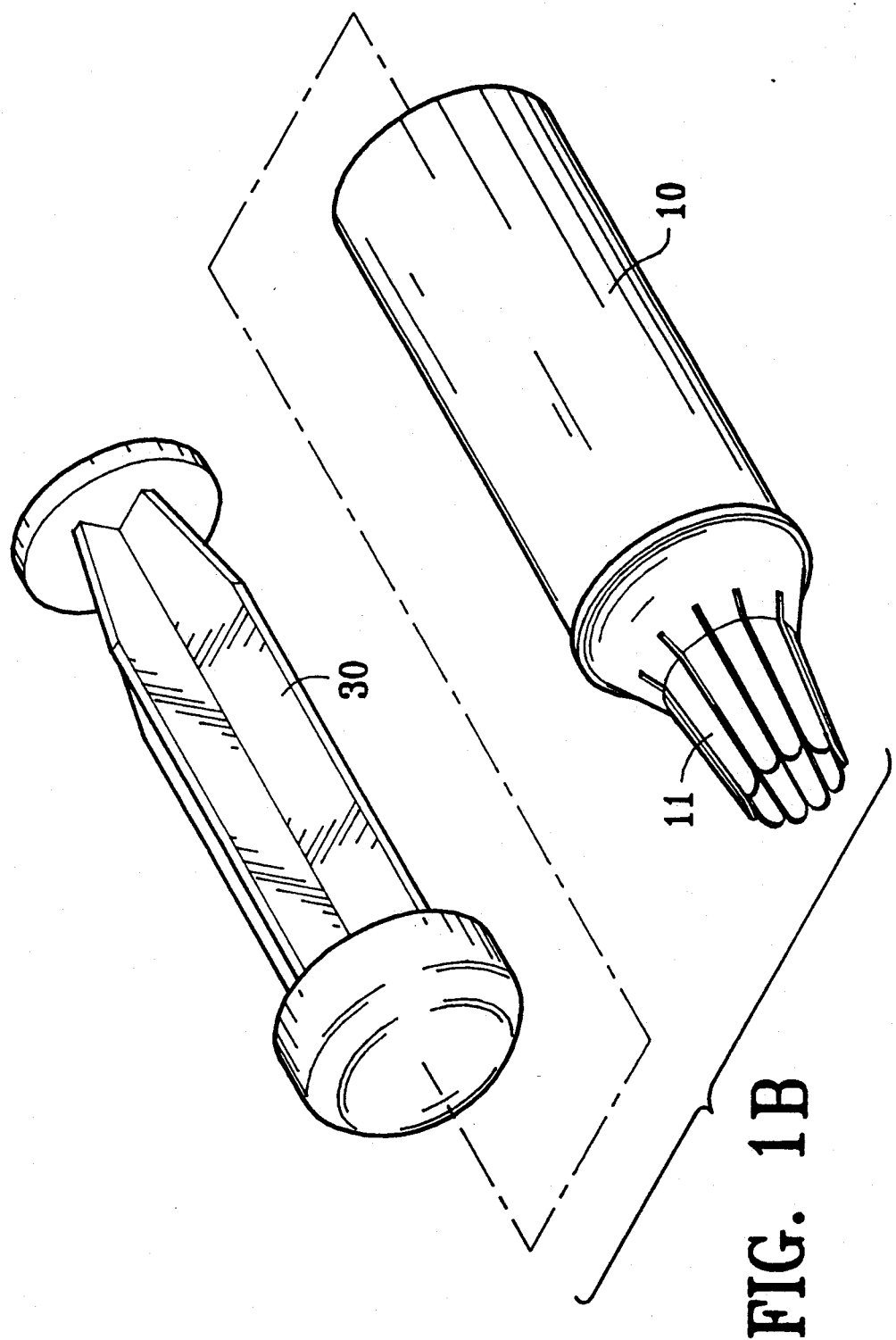
FIG. 1B is a break-down view illustrating the injector and the plunger of the present invention.

FIGS. 1A and 1B of the drawings illustrate the implant injector as comprised of a barrel 10, guiding rod 20, and a plunger 30, within the injector comprising the major feature of the present invention and integrally formed with a material offering a very good flexibility (such as polypropylene) and at the tip there are disposed twelve flaps, each being abutted to another at one end and breaking away from each other at the farther end. Each flap 11 all together, when not being subject to any external force, encompass to form an injection tip with smaller diameter.

Figure 2:
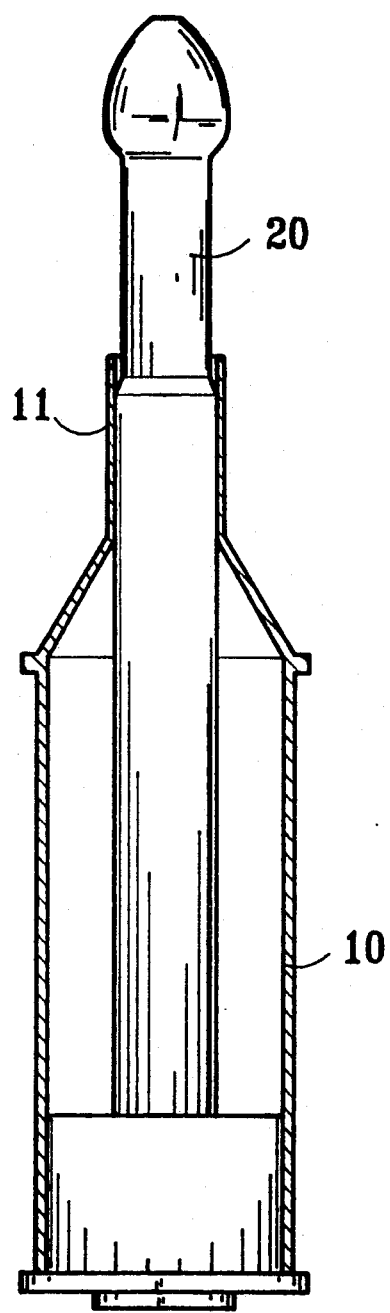
FIG. 2 is a sectional view illustrating of the assembly of the injector and the guilding rod as taken from FIG. 1A of the present invention.
Figure 3:
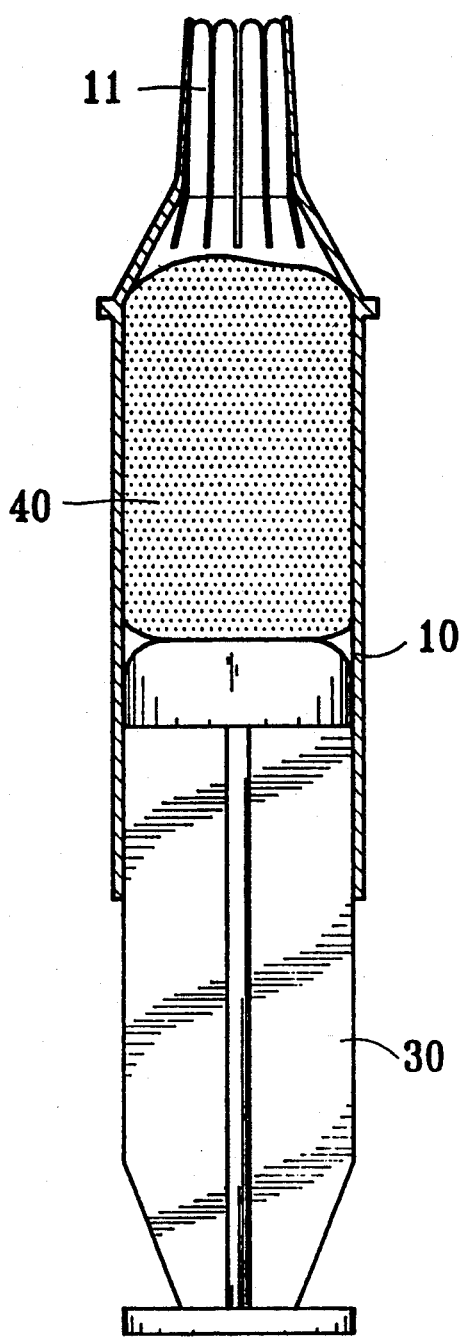
FIG. 3 is a sectional view illustrating the assembly of the injector and the plunger taken from FIG. 1B of the present invention, also the injector filled with implant material.
Figure 4:
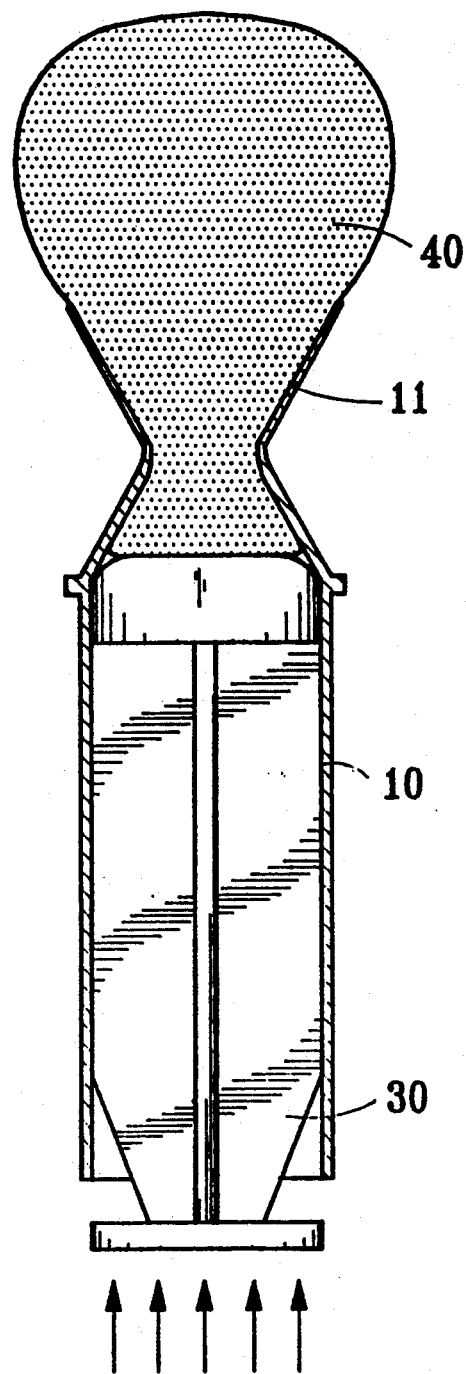
FIG. 4 is a sectional view illustrating the plunger is pushing the implant to pass through the tip of said injector of the present invention.

When mammoplasty is conducted using the present invention as illustrated in FIG. 2, said guiding rod 20 is first extending into the rear end of said injection barrel 10 in a way that the front end of guilding rod (20) provides out of the injection tip, then, with both are inserted into the incision in the skin of the patient so that the tip of barrel 10 is placed inside the incision. Later, said guiding rod 20 is pulled out to be replaced by the implant 40 inserted into the barrel 10. As illustrated in FIG. 3, the pluger 30 enters into the rear end of said barrel 10 for pushing said implant 40 through the barrel to arrive at the tip of barrel 10, where those twelve flaps 11, having being subject to the pushing force by said implant 40 will reach out as illustrated from FIG. 4 for achieving a sudden several-fold expanded diameter for said tip, thus significantly reducing the resistance encountered by said implant 40 passing through tip for making the operation an easy and fast process. After the operation, said used injecter, produced at cheap cost, is disposable to completely stop infection caused by insufficient disinfection and repeated use of the prior art. Therefore, the present invention is highly practical and safe.

With a novel configuration, the present invention allows a faster and more smooth operation compared to the prior art in the mammoplasty involving the insertion of implant while there is the major time saving; furthermore, for cheap production cost and promoted production outputs, the injector of the present invention is disposable to completely rule out the infection problem due to repeated use which requiring the disinfection in the prior art.

What is claimed is:

1. A disposable implant injector system comprising a hollow injection barrel, a guiding rod and a plunger;
said injector barrel is formed with a material having good flexibility and terminating at opposite ends, said injector barrel having at one end thereof multiple flaps forming an injection tip, each said flaps being adjacent one another in an initial state and adapted to deflect outwardly when an implant element is forced therethrough;
said guiding rod having an outer dimension to be housed within said barrel and having at one end thereof a tapered tip configured to penetrate the injection tip of the injector and an enlarged opposite end to limit the axial displacement of said rod within said barrel; and
said plunger being configured to slide freely within said barrel, said plunger having a front end adapted to push said implant within said barrel outwardly through the injection tip whereby said guiding rod is disposed within said barrel with said front end protruding outwardly from said injection tip when said injection tip is inserted into an incision in the tissue of a patient to locate the barrel in the incision, the guiding rod is removed and the implant is disposed within said barrel and said plunger is inserted into the barrel for pushing said implant therethrough to said injection tip thereby expanding said flaps and passing the implant into the tissue.

* * * * *